United States Patent [19]

Rathbun

[11] Patent Number: 4,534,467

[45] Date of Patent: Aug. 13, 1985

[54] TAMPERPROOF CAPSULE

[76] Inventor: Daniel L. Rathbun, P.O. Box 503, Hominy, Okla. 74035

[21] Appl. No.: 668,172

[22] Filed: Nov. 2, 1984

Related U.S. Application Data

[63] Continuation of Ser. No. 469,201, Feb. 24, 1983, abandoned.

[51] Int. Cl.$^3$ ........................ A61B 19/02; B65D 43/10

[52] U.S. Cl. ...................................... 206/530; 206/528

[58] Field of Search ..................... 220/8, 4 B; 206/528, 206/530, 540

[56] References Cited

U.S. PATENT DOCUMENTS 4,040,536 8/1977 Schwartz ................................ 220/8

4,128,253 12/1978 Powers .............................. 108/55.1

FOREIGN PATENT DOCUMENTS 2431672 1/1976 Fed. Rep. of Germany .......... 220/8

*Primary Examiner*—George E. Lowrance
*Attorney, Agent, or Firm*—Head, Johnson & Stevenson

[57] ABSTRACT

A self-locking, tamperproof capsule comprising hard gelatin body and cap members having essentially cylindrical sidewalls that telescopically engage to form the capsule, wherein the annular side of the telescopically engaged cylindrical surfaces contain a plurality of concentric saw-toothed protrusions that allow the filled capsule body and cap to be assembled, but prevents subsequent disassembly.

1 Claim, 2 Drawing Figures

TAMPERPROOF CAPSULE

This is a continuation of application Ser. No. 469,201 filed on Feb. 24, 1983, now abandoned.

BACKGROUND OF THE INVENTION

1. Field of the Invention

This invention relates to a tamperproof capsule. More specifically, the invention relates to a self-locking hard gelatin capsule for containing a unit dosage of medication, vitamin, pain suppressant or the like.

2. Description of the Prior Art

It is a common accepted practice to enclose or encapsulate a dosage of medication, vitamins, pain killer or the like, whether the substance be powdered, granulated or pelletized, in a hard gelatin tubular or cylindrical capsule. These capsules are usually concentric, cylindrical structures with closed ends and telescope together, thus enclosing the desired amount of material. As such, they are subject to being easily disassembled and reassembled, thus generally they are not tamperproof.

In U.S. Pat. No. 3,173,380 a separation-resistant capsule is disclosed which involves a series of inwardly raised so-called land surfaces circumferentially separated by shallow inwardly open depressions or grooves on the domed end of the outer cylindrical cap of a conventional capsule. As this cap is compressed over the other cylindrical body portion of the capsule, the land and grooves tend to distort the top of the inner cylinder, thus gripping the capsule body. In this manner, the capsule will tend to resist separation but is not totally self-locking and is not fully tamperproof. In U.S. Pat. No. 3,927,193, this same gripping engagement is again disclosed and an additional sealing band is proposed at the external junction of the telescoping concentric walls. While, in U.S. Pat. No. 4,040,536 a hard gelatin capsule having concentric cylindrical body and cap members that telescope and supposedly lock is disclosed. Again, a frictional lock is achieved because of a plurality of small axially oriented indentions inwardly directed about a circumferential ring at the top of the outer capsule member, such that a frictional resistance is created on the open end of the cylindrical body member telescopically inserted into the cap member. However to the best of the present inventor's knowledge, none of the tamper resistant capsules proposed in the prior art are truly self-locking in the sense that once assembled, the capsule must be physically broken into order to disassemble.

SUMMARY OF THE INVENTION

In view of the prior art, I have discovered an improved self-locking hard gelatin capsule which is virtually tamperproof. By placing a plurality of concentric annular saw-toothed cross-sectional locking means on both the inner surface of the capsule cap member and the outer surface of the capsule body member, the resulting capsule when telescopically assembled becomes self-locking.

Thus, the present invention provides a self-locking, tamperproof capsule comprising:

(a) a capsule body having an essentially cylindrical sidewall with one end open and the other end closed;

(b) a first saw-toothed engagement means circumferentially postioned on the outer surface of said cylindrical sidewall;

(c) a capsule cap having an essentially cylindrical sidewall with one end open and the other end closed wherein said cylindrical sidewalls of said capsule body and capsule cap are adapted to telescopically engage with each other thus forming said capsule; and (d) a second saw-toothed engagement means circumferentially positioned on the inner surface of said cylindrical sidewall of said capsule cap wherein said saw-toothed engagement means are adapted to engage with each other when said capsule body and capsule cap are telescopically assembled thus locking said capsule and wherein said first and second saw-toothed engagement means when engaged are self-destructive when forced open.

It is an object of the present invention to provide a self-locking, tamperproof capsule. It is another object that the capsule, having once been assembled, is virtually self-destructive when forceably opened, thus minimizing the risk of being reassembled. And, it is a further object that the self-locking feature be compatible with variations of internal volume of the capsule, thus allowing one capsule size to hold varying dosages of medication or the like. Fulfillment of these objects and the presence and fulfillment of additional objects will be apparent upon complete reading of the specification and attached claims taken in conjunction with the drawings.

DESCRIPTION OF THE PREFERRED EMBODIMENTS

Figure 1:
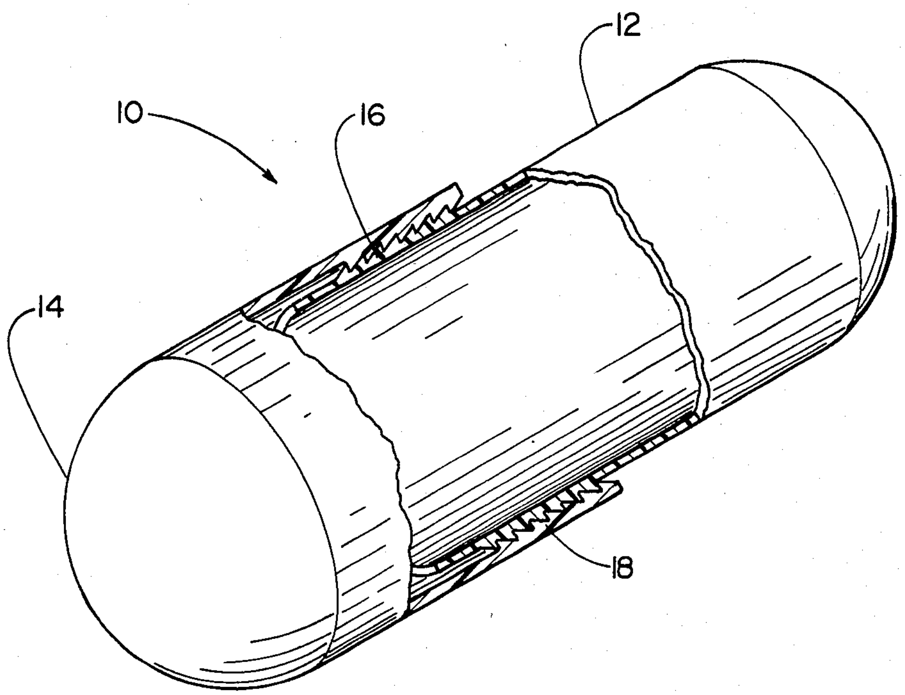
FIG. 1 is a partial cut-away perspective view of an assembled capsule according to the present invention.

The self-locking hard gelatin capsule of the present invention, how it functions and how it differs from and the advantages over the prior art capsules can perhaps be best explained and understood by reference to the drawings. FIG. 1 illustrates a partial cross-sectional view of a capsule according to the present invention, generally designated by by the numeral 10.

As illustrated, the tamperproof capsule 10 is made up of a capsule body member 12 and a capsule cap member 14. Both the cap 14 and body 12 have cylindrical sidewalls with domed ends. The cylindrical sidewalls are sized such that the body telescopically inserts into the cap, thus forming the capsule. As further illustrated, the inner surface of the cap member 14 contains a plurality of concentric molded ridges 18 with a saw-toothed cross-section wherein the teeth point or incline back towards the domed closed end of the cap 14. Similarly, the outer surface of the capsule body 12 contains a plurality of compatible concentric molded ridges 16 with complementary saw-toothed cross-sections wherein the teeth point or incline back towards the domed closed end of the body 12. Consequently, in the assembled state (see FIG. 1), the annular space between the capsule cap 14 and body 12 will be occupied by the engaged and interlocked saw-toothed structures 16 and 18.

Figure 2:
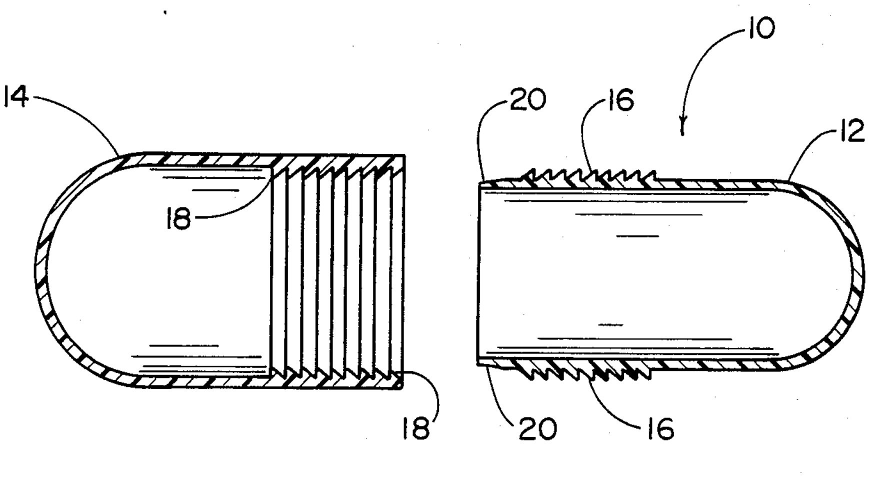
FIG. 2 is a cross-sectional view of the capsule of FIG. 1 before being filled and assembled.

As illustrated in FIG. 2, the capsule 10 in the disassembled state involves the body member 12 slightly larger in diameter than the cap member 14. The respective saw-toothed locking means (rigids 16 and 18) are molded integrally into the cylindrical sidewall of both the cap and the body. Preferably, the open ends of the body 12 are chamfered or slightly beveled for ease of assembly of the capsule. Thus, the body member 12 is equipped with a molded inclined edge 20 which assists in aligning and directing the body member 12 into the opening of cap member 14. To further assist in the alignment and ease of assembly, the cap 14 can be further equipped with an optioned beveled edge (not illustrated).

In order to assemble the tamperproof capsule of the present invention, the body member is merely filled with the appropriate desired dosage and then the cap and body are telescopically engaged and compressed, thus engaging the saw-toothed ridges. Optionally, a longitudinal groove or channel in one or both of the series of saw-toothed ridges can be used to allow air to escape during assembly of the capsule. Since the points of the teeth slip over each other during assembly, but interlock (oppose each other) when the capsule is pulled apart, once assembled the capsule cannot be disassembled. By appropriately selecting the wall thickness and dimensions, the assembled capsule can be made to essentially self-destruct if disassembly is attempted, thus additionally insuring the tamperproof feature of the present invention.

By selecting the overall respective length of the series of interlocking ridges, their relative position and the relative length of the chamfered end(s), the range of penetration of the assembled capsule body and cap can be predetermined, thus allowing for variation of the volume of the medication being enclosed in the capsule.

The capsule according to the present invention can be manufactured out of any essentially edible or digestible composition as well known in the art. Preferably, the capsule is made out of a hardenable gelatinous composition. Similarly, the method of manufacturing can be any of the methods well known in the art. Preferably, the capsule body and cap are molded by dipping mold pins into a hardenable gelatinous composition and then withdrawing the pins with a gelatin film coating on the pin. Since the saw-toothed ridges are preferably radial rings protruding from the cylindrical surface, the pin molds can be advantageously segmented to assist in removing the molded member. However, other compatible methods of fabrication of a saw-toothed structure should be considered equivalent for purposes of this invention.

Having thus described the preferred embodiment with a certain degree of particularity, it is manifest that many changes can be made in the details of construction, arrangement and fabrication of the elements without departing from the spirit and scope of the invention. Therefore, it is to be understood that the invention is not limited to the embodiments set forth herein for purposes of exemplification, but is to be limited only by the scope of the attached claims, including a full range of equivalents to which each element thereof is entitled.

I claim:

1. A self-locking, tamperproof, capsule comprising:

(a) a capsule body having an essentially cylindrical sidewall with one end open and other end closed;

(b) a first saw-toothed engagement means circumferentially positioned on the outer surface of said cylindrical sidewall;

(c) a capsule cap having an essentially cylindrical sidewall with one end open and the other end closed wherein said cylindrical sidewalls of said capsule body and capsule cap are adapted to telescopically engage with each other thus forming said capsule; and (d) a second saw-toothed engagement means circumferentially positioned on the inner surface of said cylindrical sidewall of said capsule cap wherein said saw-toothed engagement means are adapted to engage with each other when said capsule body and capsule cap are telescopically assembled thus locking said capsule and wherein said first and second saw-toothed engagement means when engaged are self-destructive when forced open.

* * * * *